(12) United States Patent
Holub et al.

(10) Patent No.: US 8,704,825 B2
(45) Date of Patent: Apr. 22, 2014

(54) METHOD FOR GENERATING A FOUR-DIMENSIONAL REPRESENTATION OF A TARGET REGION OF A BODY, WHICH TARGET REGION IS SUBJECT TO PERIODIC MOTION

(75) Inventors: Wolfgang Holub, Nürnberg (DE);
Günter Lauritsch, Nürnberg (DE);
Christopher Rohkohl, Bochum (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/314,445

(22) Filed: Dec. 8, 2011
(Under 37 CFR 1.47)

(65) Prior Publication Data
US 2012/0280978 A1 Nov. 8, 2012

(30) Foreign Application Priority Data
Dec. 14, 2010 (DE) .......................... 10 2010 062 975

(51) Int. Cl.
*G06T 15/00* (2011.01)
(52) U.S. Cl.
USPC ........................................................ 345/419
(58) Field of Classification Search
USPC .......................................................... 345/419
See application file for complete search history.

(56) References Cited

U.S. PATENT DOCUMENTS

2012/0170822 A1* 7/2012 Litvin et al. .................. 382/131

FOREIGN PATENT DOCUMENTS

EP 2242023 A1 10/2010

OTHER PUBLICATIONS

Hansis, E., et al. "Projection-based motion compensation for gated coronary artery reconstruction from rotational x-ray angiograms." Physics in medicine and biology 53.14 (2008): 3807.*
Blondel, Christophe, et al. "Reconstruction of coronary arteries from a single rotational X-ray projection sequence." Medical Imaging, IEEE Transactions on 25.5 (2006): 653-663.*
Christophe Blondel et al., "Reconstruction of Coronary Arteries From a Single Rotational X-Ray Projection Sequence", IEEE Transactions on Medical Imaging, IEEE Service Center, Piscataway, NJ, US LNKD-DOI:10.1109/TMI.2006.873224, vol. 25, No. 5, May 2006; pp. 653-663.
Eberhard Hansis et al., "Projection-based motion compensation for gated coronary artery reconstruction from rotational x-ray angiograms", Phys. Med. Biol. 53 (2008) pp. 3807-3820.

(Continued)

*Primary Examiner* — David Zarka
*Assistant Examiner* — Vu Nguyen

(57) ABSTRACT

A method for generating a four-dimensional representation of a periodically moving target region is proposed. A motion-compensated three-dimensional image dataset is determined from two-dimensional projection images recorded from different projection directions. Estimation parameters that describe a non-periodic motion and are derived from a motion model formulated independently of the phase of the periodic motion with respect to the recording instants of the projection images are determined from the projection images, such that the three-dimensional image dataset represents a static reconstruction based on all projection images for a specific instant. The three-dimensional image dataset is animated from the estimation parameters used in its reconstruction. The motion information that is missing in the estimation parameters due to the two-dimensionality of the projection images is additionally determined using a boundary condition that describes the periodicity of the motion, and used for the animation.

9 Claims, 1 Drawing Sheet

(56) References Cited

OTHER PUBLICATIONS

Christopher Rohkohl et al., "C-arm CT: Reconstruction of Dynamic High Contrast Objects Applied to the Coronary Sinus", 2008 IEEE Nuclear Science Symposium Conference Record, M10-328, pp. 5113-5120, Dresden, Germany, Oct. 2008.

Eberhard Hansis et al., "High-quality 3-D coronary artery imaging on an interventional C-arm x-ray system", Med. Phys. 37 (4), Apr. 2010, pp. 1601-1609.

Christopher Rohkohl et al., "ECG-Gated Interventional Cardiac Reconstruction for Non-periodic Motion", MICCAI 2010, Part I, LNCS 6361, pp. 151-158.

Dirk Schäfer et al., "Three-dimensional reconstruction of coronary stents in vivo based on motion compensated X-ray angiography", Proc. SPIE 6509, 65091M (2007).

* cited by examiner

METHOD FOR GENERATING A FOUR-DIMENSIONAL REPRESENTATION OF A TARGET REGION OF A BODY, WHICH TARGET REGION IS SUBJECT TO PERIODIC MOTION

CROSS REFERENCE TO RELATED APPLICATIONS

This application claims priority of German application No. 10 2010 062 975.8 filed Dec. 14, 2010, which is incorporated by reference herein in its entirety.

FIELD OF INVENTION

The invention relates to a method for generating a four-dimensional representation of a target region which is subject to periodic motion, wherein a motion-compensated three-dimensional image dataset is determined from a plurality of two-dimensional projection images that have been recorded from different projection directions, wherein estimation parameters which describe a non-periodic motion and are derived from a motion model that is formulated independently of the phase of the periodic motion with respect to the recording instants of the projection images are determined on the basis of the projection images, such that the three-dimensional image dataset represents a static reconstruction for a specific instant, said static reconstruction being based on all projection images.

BACKGROUND OF INVENTION

Image reconstruction methods in which a three-dimensional image dataset is determined from a multiplicity of two-dimensional projection images that were recorded in different recording geometries, i.e. from different projection directions, are well known in the prior art. Iterative reconstruction methods or filtered back-projection methods can be used, for example. Problems always occur when the recording volume (i.e. the target region) moves, as in the case of target regions surrounding the heart, for example.

After originally using motion estimation methods that already include in principle the assumption of periodicity in the case of target regions of a body that are subject to periodic motion, satisfactory reconstruction quality was still found to be lacking. This is explained by the fact that the various instances of periodic motion nonetheless exhibit small differences, which have a negative influence on the reconstruction quality.

Surprisingly, it was found that the reconstruction quality can be significantly improved using non-periodic motion models, i.e. it is taken as a starting point that a non-periodic motion will be estimated, wherein said non-periodic motion can be used in a dynamic reconstruction algorithm (such as those that are already well known) in order to obtain a significantly improved reconstruction image, i.e. an artifact-free three-dimensional image dataset of higher quality. A method of the type cited in the introduction is disclosed in EP 2 242 023 A1, for example. This describes a method for the motion-compensated reconstruction of a three-dimensional definitive reconstruction dataset of a recording volume (which moved during a recording period) from two-dimensional projection images, using a dynamic and in particular analytical reconstruction algorithm, wherein for the purpose of determining the in particular location-dependent non-periodic motion during the recording time, an initial parameter set describing a possible motion in at least one motion model, in which the time dependency is described by the recording time, is first defined as a current parameter set, whereupon, in the context of an optimization method relating to the parameter set, a current reconstruction dataset is determined by means of the dynamic reconstruction algorithm with reference to the possible motion described by the current parameter set and is evaluated on the basis of a target function which comprises an evaluation measure, such that when a convergence criterion for the target function is finally satisfied, the optimization method can be terminated and the current reconstruction dataset can be used as the definitive reconstruction dataset. The definitive reconstruction dataset, which was already reconstructed during the optimization method, therefore corresponds to the three-dimensional image dataset of the present invention.

The method disclosed in EP 2 242 023 A1 therefore uses a parameterizable non-periodic motion model, which is therefore not defined by phases of a periodic motion but by the current time, such that recording times or the recording instant can be used immediately, without requiring a periodic motion as a basis. Various embodiments are conceivable in respect of the target function, wherein both comparison with a three-dimensional reference dataset and comparison with the recorded projection images are possible, wherein forward-projection images can be determined from the current reconstruction dataset using dynamic forward projection, and their similarity to the actual recorded projection images can be evaluated. As mentioned above, the overall result is a significant improvement in quality of the three-dimensional image dataset of the target region. Optimal image quality is achieved when the generated static three-dimensional image correlates to a heart phase in which the heart is almost at rest, usually the end-diastolic phase, and also in the systolic rest phase in the case of rapid heartbeats. A non-periodic approach to the motion makes it possible at least significantly to reduce those serious impairments to the image quality that are caused by heart phases involving pronounced motion, e.g. the systolic contraction or the early diastolic dilatation.

The resulting three-dimensional image datasets, which can show e.g. the coronary arteries and the heart, are an extremely useful tool, e.g. in the planning of minimally invasive interventions, in particular using a catheter, but also for image monitoring during an intervention, when the three-dimensional image dataset is superimposed by fluoroscopy images. However, there is also considerable demand in general for four-dimensional information in this context, i.e. for a moving representation of a target region, in particular the heart region, since such four-dimensional information is useful for functional analyses and dynamic overlapping. In interventions for clearing a chronic total occlusion, for example, such moving superimpositions of images therefore provide an extremely useful aid for the navigation of a catheter through the occluded part in order to clear the occlusion by means of ablation, for example, and reduce the risk of harming or even rupturing the vessel.

Previously disclosed are merely methods in which dynamic information is generated by an electrocardiogram gating for a corresponding heart phase. The image result of the ECG gating is post-processed, e.g. by compensating for the residual motion, wherein a 4D animation of a heartbeat is provided by separate three-dimensional reconstruction of various heart phases. Due to the problems cited above in respect of the assumption of a periodic motion, and the fact that a separate three-dimensional image dataset must be specified at considerable computing cost for each heart phase, the resulting pictures are of extremely poor quality and suffer from all manner of artifacts and other quality deficiencies, and are therefore very difficult to read.

The article "High-quality 3-D coronary artery imaging on an interventional C-arm x-ray system" by Eberhard Hansis et al., Med. Phys. 37 (4), April 2010, pages 1601 to 1609, concerns the projection-based motion compensation for the reconstruction of coronary arteries in a single heart phase using a gating.

The article "ECG-Gated Interventional Cardiac Reconstruction for Non-periodic Motion" by Rohkohl et al., MICCAI 2010, Part I, LNCS 6361, pages 151 to 158, likewise describes an electrocardiogram-gated reconstruction algorithm, in which a weighting factor is used for the images of a specific heart phase. The result is a three-dimensional image dataset in a specific heart phase.

The article "Reconstruction of Coronary Arteries From a Single Rotational X-Ray Projection Sequence" by Christophe Blondel et al., IEEE TRANSACTIONS ON MEDICAL IMAGING, Vol. 25, No. 5, May 2006, pages 653 to 663, discloses a reconstruction of coronary arteries from a single projection sequence, wherein an estimation of the motion of the coronary arteries is carried out. The tomographic reconstruction of the coronary arteries includes motion compensation and is three-dimensional.

SUMMARY OF INVENTION

The invention therefore addresses the problem of specifying an improved method for depicting the three-dimensional motion of a target region.

In order to solve this problem, it is inventively proposed that, in the context of a method of the type cited in the introduction, the three-dimensional image dataset should be animated on the basis of the estimation parameters of the non-periodic motion model that were used in its reconstruction, wherein the motion information that is missing in the estimation parameters due to the two-dimensionality of the projection images is additionally determined using a boundary condition that describes the periodicity of the motion, and is used for the animation.

The present invention is therefore based on the three-dimensional image dataset which represents a static reconstruction at a specific instant, said static reconstruction being based on all projection images, and the estimation parameter set that describes the non-periodic motion in the non-periodic motion model. Both can be obtained as described in EP 2 242 023 A1, for example, wherein other approaches are naturally also conceivable. As mentioned previously, the three-dimensional image dataset is of high quality, while the estimation parameters describe the non-periodic motion in the motion model. In order now to achieve a dynamic imaging in accordance with the invention, the static three-dimensional image dataset is determined using optimal image quality and is animated using the field of motion that is known from the reconstruction step, said field of motion being described by the estimation parameters. Therefore the excellent image quality of the static three-dimensional image dataset is used in order to obtain an easily readable and clear dynamic representation of the target region, since in fact the image quality of the static three-dimensional image dataset is continuously maintained. As a result of this analysis of the measured data, i.e. the projection images, it is therefore possible to create an extremely useful aid for planning interventions and possibly also for diagnosis.

In this case, the present invention also allows for a problem which originates from the fact that the estimation parameters in the non-periodic motion model are determined on the basis of the two-dimensional projection images. The individual projection images are recorded consecutively at specific instants and cannot necessarily capture the motion components that are perpendicular to the projection plane. This means that information relating to the motion that is perpendicular to the projection plane is ultimately missing for each projection image (or the corresponding instant). However, this information is required for the animation to be complete and correct, and therefore the inventive method for solving this problem specifically proposes that the motion information that is missing in the estimation parameters due to the two-dimensionality of the projection images should additionally be determined using a boundary condition that describes the periodicity of the motion, and used for the animation.

It is therefore proposed that the spatial components which, due to insufficient measured data, are missing in the 4D field of motion as described by the estimation parameters should be obtained by means of the boundary condition of a periodic motion. The fundamental idea here is that the acquisition of the projection images generally takes place over a plurality of cycles of the periodic motion, e.g. a plurality of heart cycles, and therefore projection information from different directions is in fact available again for a phase in the context of a periodic observation, making it possible to determine the missing spatial components. In this case, it should be emphasized here that the retrospective assumption of a periodic motion for generating the 4D animation is more advantageous than already postulating a periodic motion during the calculation of the static three-dimensional image dataset, since the image quality of the static three-dimensional image dataset is clearly better, as described above. Inconsistencies and/or errors due to non-periodic motion components therefore affect the animation only, but do not influence the static three-dimensional image on which the animated display is based, such that representation quality is not reduced at all.

The estimation parameters that are derived from the reconstruction step, i.e. the estimated field of motion, therefore contain a missing spatial component in the direction of the recording x-ray beam, said missing component being derived on the basis of the retrospective assumption that the field of motion is periodic, in particular periodic in the heartbeat. Because the time is used for the purpose of parameterization in the context of the non-periodic motion model, each instant is assigned a corresponding heart phase, wherein the periodicity in the field of motion results in the approximation that the same motion vectors were measured at different instants in different projection directions but in the same heart phase. The direction of the missing spatial components changes as a result of the different projection angles, and therefore the missing spatial components can be specified from the plurality of measurements.

In a preferred embodiment of the present invention, provision can be made in this case for motion parameters of a periodic motion model to be specified in an optimization method such that a target function is minimized, said target function describing the agreement of the motion that is described by the currently defined motion parameters with the motion that can actually be derived from the position images and is determined from the estimation parameters, wherein the definitive motion parameters that minimize the target function are used for the animation.

The calculation of the complete, now periodic four-dimensional field of motion can be formulated as an optimization problem concerning a periodic motion model. The objective is to select the parameters describing the motion in the periodic motion model in such a way that the motion which can actually be described by the projection data of the projection images is reproduced as precisely as possible. This means that a target function is formulated which ultimately describes the extent to which the actual measured spatial components agree with the corresponding components which are derived from the periodic motion model. In other words, the optimization method attempts to find a periodic four-dimensional field of motion whose projections are identical to those of the non-periodic field of motion as derived from the projection images and described by the estimation parameters.

In this case, provision can be made for the motion that can actually be derived from the projection images to be determined by projecting the motion that is determined from the estimation parameters for a specific motion phase onto a plane, in particular a detector plane, which is defined by at least one recording geometry of the at least one projection image that is assigned to the motion phase, and which is perpendicular relative to the projection direction. Provision is therefore made for determining actual or at least estimated recording geometries that define a plane on which both the motion vector that is described by the estimation parameters and the motion vector that is described by the current motion parameters are projected, in order that they can then be compared with each other. In this case, it should be emphasized here that not only actual recording instants of the projection images can be observed, but that intermediate states can also be observed, using interpolation if applicable. In the non-periodic motion model, the motion can be specified for any instant and not just for discrete instants. Depending on the model that is used, various projection images (in particular the adjacent projection images) are therefore relevant at this instant. If, as is preferred, the phase of the periodic motion is now observed continuously, e.g. as a value between 0 and 1, it is unlikely in principle that two actual recorded projection images will relate to exactly the same heart phase, and therefore an "unconnected" observation appears useful even if only several discrete heart phases are observed. If a recording geometry is to be specified for these instants which correspond to the heart phase, a continuous recording path is then determined, e.g. by means of interpolation from the existing discrete actual recording geometries, and is used for determining the plane that is perpendicular to the projection direction. Nevertheless, provision can be made for phases which correspond to actual recording instants to be selected as the phases of periodic motion that are to be observed, i.e. for taking into consideration the corresponding phase of the periodic motion at the recording instant of each projection image.

A projection can take the form of an orthogonal projection or a perspective projection. An orthogonal projection is appropriate if the images were recorded in the parallel beam geometry, while the perspective projection is preferred if the images are recorded in the fan beam geometry.

The assignment of instants in the non-periodic motion model to a motion phase in the periodic motion model can be effected with reference to an electrocardiogram that was recorded when the images were recorded and/or with reference to the periodicity information that was determined on the basis of the estimation parameters. The mapping of the instants, which effectively parameterize the non-periodic motion model, onto phases, in particular continuously defined phases, of the periodic motion can therefore be effected with reference to measurement information from a recorded electrocardiogram, for example. It is naturally also conceivable to analyze the motion that is described by the estimation parameters in the non-periodic motion model in respect of its periodicity, and to derive the motion information from this, such that an additional measurement from an electrocardiogram is no longer necessary in this case.

In a further embodiment of the invention, provision can be made for using a four-dimensional spline model as a motion model, preferably using cubic B-spline base functions in particular. In this way, location-dependent motions can be described locally, wherein such a description for the heart motion is already proposed in the references. Spline models describe a motion that is smooth in relation to location and time, particularly if cubic B-spline base functions are used. If such a spline model is used, control points are usually assigned to displacement vectors. In the context of the method according to the invention, these displacement vectors or their components can then form the motion parameter set that is to be optimized. However, other periodic motion models are also conceivable.

With regard to the optimization method, provision can be made for using a gradient-based optimization method, for example. Various approaches are likewise conceivable here, however, since optimization methods are generally well known in the prior art and need not be explained in further detail here.

BRIEF DESCRIPTION OF THE DRAWINGS

Further advantages and details of the present invention are revealed by the exemplary embodiments described below and with reference to the drawing, in which.

DETAILED DESCRIPTION OF INVENTION

Figure 1:
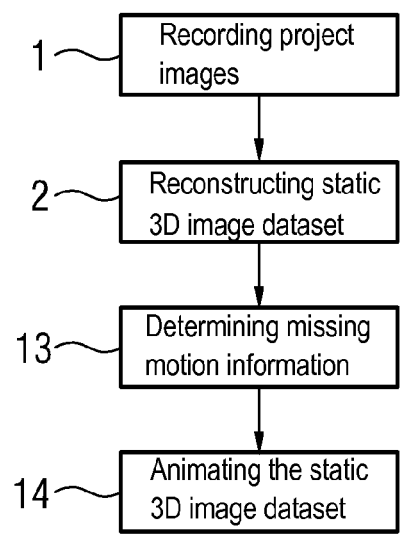
FIG. 1 shows a flow diagram of the method according to the invention.

FIG. 1 shows a flow diagram of the method according to the invention. In a step 1, provision is made for recording projection images which, in the exemplary embodiment that is represented here, show the coronary vessels and the heart from different projection directions. The recording lasts for several heart cycles in this case. An electrocardiogram is recorded using a suitable measuring device at the same time as the projection images.

In a step 2, the dynamic reconstruction of a static three-dimensional image dataset from the two-dimensional projection images now takes place, wherein a non-periodic motion model is used and is adapted in an optimization method to at least some of the actual recorded projection images. Specifically, provision is made for determining a current reconstruction dataset in a dynamic reconstruction method, in particular an FDK method, during each step in an optimization method. From this, projection images are then determined by means of dynamic forward projection, and compared with the actual recorded projection images until they correspond to the latter as exactly as possible. It should be noted here that provision can obviously be made for other evaluation rules in other exemplary embodiments, e.g. the comparison with a reference dataset.

Details of such a procedure can be found e.g. in the previously cited EP 2 242 023 A1, which is included in its entirety in the disclosure of the present invention with regard to the details of this determination method.

The determinations in step 2 therefore result in an optimal reconstruction dataset, subsequently referred to as a three-dimensional image dataset, and estimation parameters which describe the non-periodic motion in the non-periodic motion model. During the further course of the inventive method, a dynamic representation of the heart and the coronary vessels must now be generated, for which purpose the motion described by the estimation parameters cannot be used directly, however, due to the existence of a problem which is solved by the present invention. Concerning this, reference is made to the illustration in FIG. 2.

This shows two projections 3, 4 of a motion 5, which is broken down into orthogonal components 6, 7 and 8 here. Corresponding positions of radiation sources are denoted by 9 and 10, the fan beam geometry being illustrated here.

If the motion 5 is recorded solely from the projection direction that is associated with the projection plane 3, it is clear that only the components 6 and 7 are depicted. Similarly, only the components 6 and 8 of the motion 5 can be seen in the other projection direction, this being perpendicular to the first.

If a non-periodic motion is therefore estimated on the basis of two-dimensional projection images, the motion component along the direction of the x-radiation is missing at each instant, since said x-radiation cannot be identified in the corresponding projection planes 11, 12 (e.g. the detector planes).

If the static three-dimensional image dataset determined in step 2 is now to be animated on the basis of the estimation parameters, the missing motion information must be determined. According to the invention, this is now done using a periodic motion model in step 13 (FIG. 1), wherein the motion parameters of the periodic motion model are specified in such a way that they agree as exactly as possible with the motion (i.e. the corresponding motion components) that can be inferred from the two-dimensional measured data (projection images).

Equation (1) describes the parameterization of the non-periodic motion model that is used in step 2, $$x_t = x + \Delta x_t = x + B(t, x, s) \tag{1}$$

where x describes a three-dimensional position vector and $x_t$ describes the new position vector at the instant t in the time after the motion with the vector $\Delta x_t$. B designates the motion model with the estimation parameter vector s at the position x.

As explained above with reference to FIG. 2, however, only those motion components that are perpendicular to the x-ray beam direction, i.e. the projection direction, can be determined at a recording instant t. These components $u=(u,v)^T$ can be specified using the same projection operation P(t,x) as in the image recording.

$$u = \begin{pmatrix} u \\ v \end{pmatrix} = P(t, x + \Delta x_t) = P(t, x + B(t, x, s)) \tag{2}$$

P(t,x) therefore projects a vector x onto the projection plane (cf. 11, 12 in FIG. 2) in which the recording is or was made at the instant t, since the concept can be applied to the continuous case, i.e. every instant t, if the recording positions are interpolated to form a recording path.

In this case, however, motions of a number N of transformed coordinates are now used as an input for the motion which the new periodic motion model is to reproduce, and are used as the measured results which the periodic motion model is to describe:

$$u_n \stackrel{!}{=} P(t_n, x_n + B_{periodic}(h(t_n), x_n, s_{periodic})). \tag{3}$$

In this case, $B_{periodic}$ is the time-periodic motion model by means of which the coordinate $x_n$ (where n is in the range 1-N) is moved to a new position during the relative heart phase $h(t_n)$. The heart phase here is specified as a continuous parameter between 0 and 1 in this case. The periodic motion model is described by the motion parameter $s_{periodic}$ and should now be in agreement with the actual measured components of the non-periodic motion.

Due to their simpler representation, the equation systems that are produced for the orthogonal projection (i.e. the parallel beam geometry) are shown below, wherein similar equation systems can also be derived for the perspective projection. The orthogonal projections result in simple projection matrices $P_n$ having dimensions of 2×3 on the projection planes at a recording time $t_n$. As a result of this, the projections of the motion vectors are spatially invariant and compact formulas for the equation system are produced:

$$\hat{u}_n \stackrel{!}{=} P_{orthogonal}(t_n, B_{periodic}(h(t_n), x_n, s_{periodic})). \tag{4}$$

The non-periodic field of motion is observed at M points $(x_n, t_n)$ in space and time, wherein motion parameters $s_{periodic}$ should be specified such that the projections of the periodic field of motion consistently agree with the measured projections $\hat{u}_n$ of the non-periodic motion model, described by the estimation parameters. In order to specify these motion parameters $s_{periodic}$ of the periodic motion model, the expression of the equation (1) is used in order to formulate a linear equation system of N equations for all observed space-time points, which system can be described by a matrix equation:

$$y = \begin{bmatrix} \hat{u}_1 \\ \hat{u}_2 \\ \vdots \\ \hat{u}_N \end{bmatrix} = \begin{bmatrix} P_1 \\ P_2 \\ \vdots \\ P_N \end{bmatrix} \cdot B_{periodic} \cdot s_{periodic} \tag{5}$$

$$s_{periodic} = \underset{s_{periodic}}{\operatorname{argmin}} \| PB_{periodic} \cdot s_{periodic} - y \|_2$$

wherein the measurement vector y is composed of the vectors $\hat{u}_n$. The unknown is the vector $s_{periodic}$ of the motion parameters. $B_{periodic}$ generates the periodic field of motion for $(x_n, h(t_n))$. $P_n$ is the projection matrix at the instant $t_n$. The system matrix $PB_{periodic}$ is the product of the matrix B of the projection matrices $P_n$ and the matrix $B_{periodic}$.

In this exemplary embodiment of a minimization method, provision is made for normalizing the $L_2$ noun of the error, said norm being the length of the difference vector between projected periodic and non-periodic motions. Cubic four-dimensional B-splines are used in the periodic motion model, such that each motion vector $\Delta x_n$ is influenced by just three components of $s_{periodic}$ for each dimension. The matrix is therefore thinly populated, since it only has 81 entries in each row. The algorithm that is used outputs a solution for $s_{periodic}$, which has the fewest errors over all N observed instants.

In this case, 2×N equations are used in order to determine the $3 \cdot c_s^3 \cdot 3c_h$ unknowns, where $c_s$ and $c_h$ represent the number of control points for the B-spline model in the spatial dimensions and during the heart phase. Since all information from all possible perspectives, i.e. projection directions, should be taken into consideration, and it should be ensured that not too few points are observed, provision is made in this exemplary embodiment for using equations from each actual recorded projection direction, i.e. for each instant at which a projection image was recorded.

Figure 2:
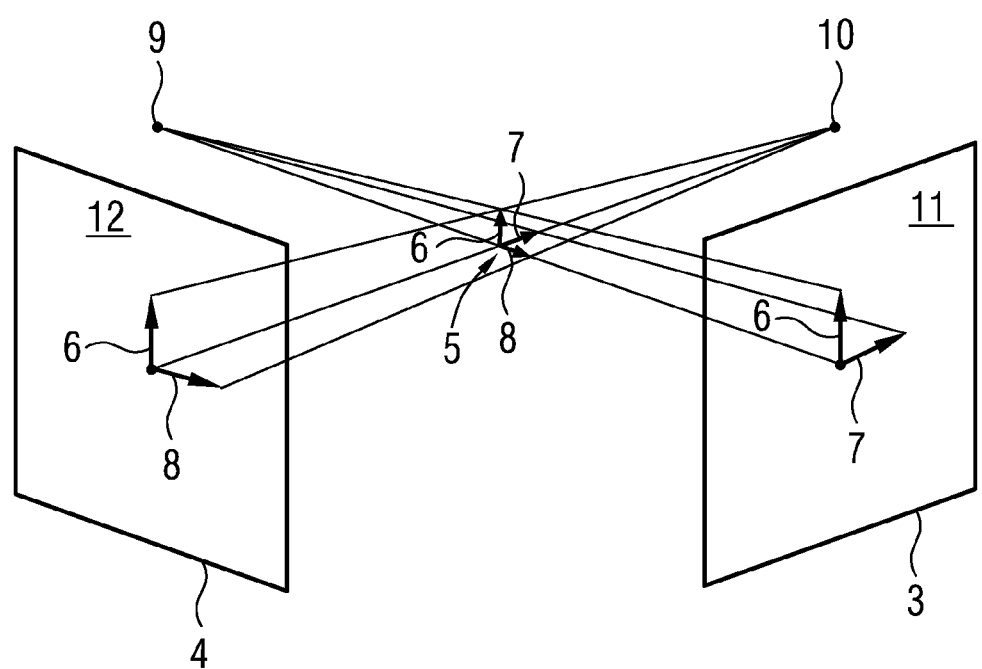
FIG. 2 shows a drawing of the underlying principle of the present invention.

In this way, the contributions of a plurality of projection images at the different heart phases can be combined, such that information is ultimately complementary as indicated in FIG. 2. In the spatial dimensions, the same arrangement of control points is used as in the non-periodic motion model. This ultimately results in a far greater number of equations than unknowns, and therefore a corresponding solution method can be used. In this context, appropriate methods are those which are suitable for overspecified systems and at the same time take advantage of the matrix being thinly populated. It is thus possible to create a robust and computationally simple solution which requires few computing resources.

The result is therefore an optimal motion parameter set for the periodic motion model, which is used in a step 14 to animate the static three-dimensional image dataset that was determined in step 2 and hence to represent the motion of the heart and the coronary arteries during a heart phase.

The invention claimed is:

1. A method for generating a four-dimensional representation of a target region subject to a periodic motion, comprising:
   reconstructing a three-dimensional image dataset from a plurality of two-dimensional projection images recorded from different projection directions at different recording instants by a computing device, wherein the three-dimensional image dataset represents a static reconstruction based on all the plurality of two-dimensional projection images for a specific instant;
   determining an estimation parameter based on the projection images by the computing device, wherein the estimation parameter describes a non-periodic motion in a non-periodic motion model and is derived from a periodic motion model that is formulated independently of a motion phase with respect to the recording instants;
   determining motion information that is missing in the estimation parameter due to the two-dimensionality of the projection images using a boundary condition describing the periodicity of the motion by the computing device;
   animating the three-dimensional image dataset based on the estimation parameter of the non-periodic motion model and the motion information by the computing device;
   breaking two of the projection images acquired at two different recording instants into orthogonal motion components on two projection planes, wherein the orthogonal motion components comprise motion parameters of the periodic motion model, wherein a motion parameter of the periodic motion model that is along a projection direction is missing at one of the two projection planes respectively, wherein the missing motion parameter of the periodic motion model is determined from the two-dimensional projection images, and wherein the periodic motion model described by the motion parameters is in agreement with the non-periodic motion model; and
   combining the orthogonal motion components of the two projection images for determining the motion information.

2. The method as claimed in claim 1,
   wherein the missing motion parameter of the periodic motion model is defined in an optimization method to minimize a target function and is used for the animation, and
   wherein the target function describes an agreement of the motion that is described by the defined motion parameter with the motion that is derived from the projection images and is determined from the estimation parameter.

3. The method as claimed in claim 2,
   wherein the motion that is derived from the projection images is determined by projecting the motion that is determined from the estimation parameter for a specific motion phase onto a plane,
   wherein the plane is defined by at least one recording geometry of at least one of the projection images that is assigned to the specific motion phase, and
   wherein the plane is perpendicular relative to a direction of a projection.

4. The method as claimed in claim 3, wherein the plane is a detector plane.

5. The method as claimed in claim 3, wherein the projection comprises an orthogonal projection or a perspective projection.

6. The method as claimed in claim 3, wherein the specific motion phase is taken into consideration at the recording instant of each projection image.

7. The method as claimed in claim 1, wherein an instant in the non-periodic motion model is assigned to the motion phase with reference to an electrocardiogram recorded when recording the project images and/or with reference to the periodicity information determined based on the estimation parameter.

8. The method as claimed in claim 1, wherein the periodic motion model comprises a four-dimensional spline model.

9. The method as claimed in claim 8, wherein the four-dimensional spline model is determined using cubic B-spline base functions.

* * * * *